United States Patent [19]
Subrini

[11] Patent Number: 6,015,380
[45] Date of Patent: Jan. 18, 2000

[54] EXTRA-CAVERNOSAL PENILE IMPLANTS

[76] Inventor: Louis Subrini, 5 Rue Emmanuel Chabrier, 78370 Plaisir, France

[21] Appl. No.: 09/042,281

[22] Filed: Feb. 5, 1998

Related U.S. Application Data

[63] Continuation of application No. 08/579,825, Dec. 28, 1995, abandoned.

[30] Foreign Application Priority Data

Dec. 28, 1994 [FR] France .................................. 94-15763

[51] Int. Cl.$^7$ ........................................................ A61F 5/00
[52] U.S. Cl. .................................. 600/40; 600/38; 600/39
[58] Field of Search .................................. 600/38, 39, 40

[56] References Cited

U.S. PATENT DOCUMENTS 5,088,477  2/1992  Subrini ........................................ 600/40

*Primary Examiner*—Linda C. M. Dvorak
*Assistant Examiner*—Rosiland Kearney
*Attorney, Agent, or Firm*—Larson & Taylor

[57] ABSTRACT

The invention concerns an extra cavernosal penile implant which can be used to increase penile volume. The implant includes two cheeks independent from one another which are adapted to cover the outer lateral sides of the corpus cavernosum without covering the upper and lower sides thereof. Each of the cheeks has a crescent-shaped or hemi-cylindrical vertical cross-section. Each cheek also includes a distal end which is adapted to conform to the anatomy of the sulcus of the glans and includes for this purpose an oblique planar end surface which slants from the distal end toward the proximal end of the implant in a direction from the outer surface to the inner surface of the implant which is designed to cover the corpus cavernosum.

10 Claims, 1 Drawing Sheet

EXTRA-CAVERNOSAL PENILE IMPLANTS

This is a continuation of application Ser. No. 08/579,825 filed Dec. 28, 1995, now abandoned.

The present invention concerns an extra-cavernosal penile implant designed to increase penile volume.

Current techniques for this purpose involve using insertion of fat under the skin of the penis, which presents multiple disadvantages:

1. The fat has a strong tendency to cause inflammation, which often leads to rejection, or obliges removal of the fat.
2. The necrosis of the fat, even if it is partial, results in a strong diminution of its initial volume.
3. The length of the penis is not significantly increased.

It is also possible to increase the volume of the penis by inserting an all-purpose penile prosthesis. The disadvantage in that case is that prosthesis is inserted into the corpus cavernosum which is the organ of erection, with the evident risk of leading to impotence.

It is also possible to insert an odd and median prosthesis under the skin. In that case the prosthesis must be only of a weak section, and will not significantly increase the volume, except if it is of a large cross section. In that case the penis would be higher than broad, which is the opposite of the normal anatomy. Another disadvantage of such a prosthesis, is that the distal pressure area of the prosthesis at the level of the glans would be located only at the level the dorsal side, without any lateral support and with the risk of deformation of the glans, or perforation due to excess pressure. Globally, known penile prostheses are designed to allow penetration for impotent patients, and not to increase the volume of the penis in individuals with a normal erection.

The present invention plans to remedy the inconvenience and insufficiencies of the above techniques.

The goal of the invention is to increase the total volume of the penis by increasing both its diameter and its length, using a penile implant which covers a part of the corpus cavernosum, in its penile part, or "penis pendulum."

The penile implant according to a first characteristic, comprises two independent cheeks, which cover the corpus cavernosum, without covering the upper and lower sides. The cross section of each cheek is preferably crescent like, as illustrated in FIG. 1.

According to particular modes of realization of the invention:

The distal edge can be located in an oblique plane which is in relation to the long axis of the implant.

The device can include perforations.

The two cheeks may be connected one to the other by a thin sheet.

The device may present one or several areas of a material secondarily penetrated by neighbor tissues.

The annexed drawings illustrate the invention.

Figure 1:
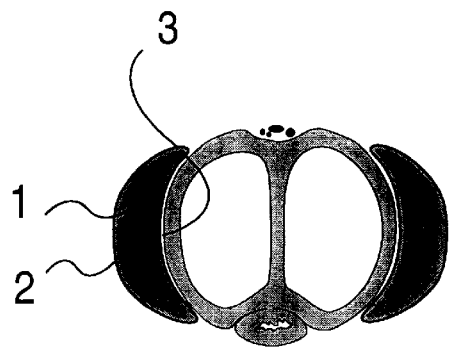
FIG. 1 represents a section of the device according to the invention.

In reference to these drawings, the penile implant according to a first embodiment is made of two cheeks, one left and the other right, independent from one another, whose transverse section is crescent-shaped. The outer side 2 is convex, and the inner side 3 is concave as represented in FIG. 1. The concavity can be more or less pronounced, and can even be null, the inner side 3 becoming flat, the cheek having then the shape of half a cylinder, not shown. The two cheeks are located laterally on each side of the corpus cavernosum in order to cover its lateral side without covering upper and lower sides.

The edges may be left free, or sutured to the corpus cavernosum, either directly, or by the intermediary of a strengthening strip.

Figure 3:
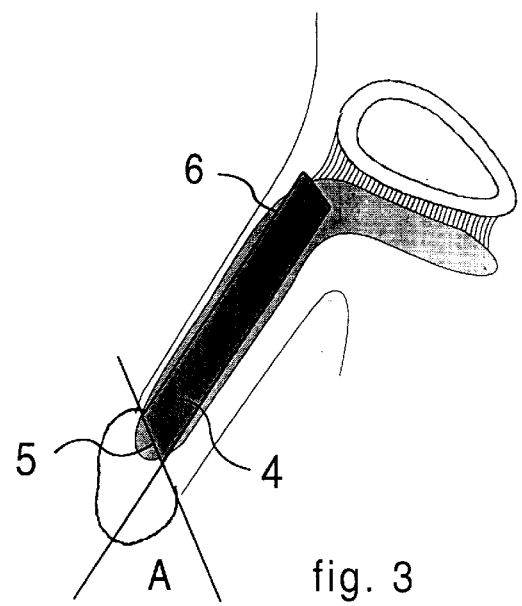
FIG. 3 represents a left lateral view of the left cheek, inserted into the penis.
Figure 2:
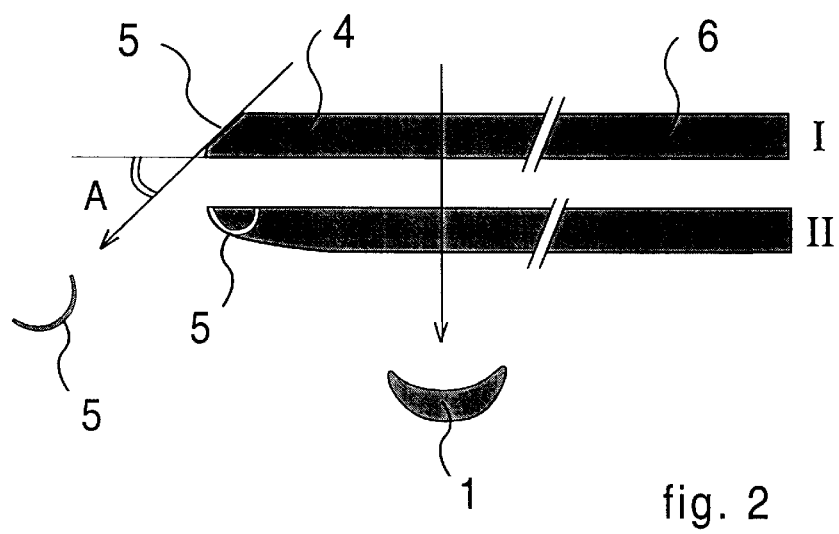
FIG. 2 represents a lateral view of the left cheek: in left view I, and in upper view II, as well as two cross sections at different points.

Each implant presents a distal extremity and a proximal extremity. The distal extremity 4 can include a progressive diminution of its thickness as illustrated in FIG. 2. The free edge 5 of the distal extremity may be cut in oblique at the expense of its upper edge, according to an angle A of about 45°, in order to conform to the anatomy of the sulcus of the glans on which it is supported, as shown in FIGS. 2 and 3. The proximal extremity 6 uses an opposed support at the level of the suspensory ligament of the penis. This extremity 6 may be cut by the surgeon to the desired length, in order to get a tailor-made implant. If measurement is taken on an extended penis, the device permits an increase of the length of the penis at rest, which is added to the increase of diameter to realize an important increase of the total volume.

The device is made from a bio-compatible material. It may be full and homogeneous and of a hardness comprised between about 25 and 50 shore A. It also may be made from a gel or analogous material. In this last case, it is surrounded by an appropriate sheath.

According to one of the modes of invention, the device may include one or several areas made from a fabric like DACRON polyester for example. The fabric will be then penetrated by neighbor tissues thereby preventing any secondary displacement of the device. The strengthening strip (not represented) may be made from such a fabric.

Figure 4:
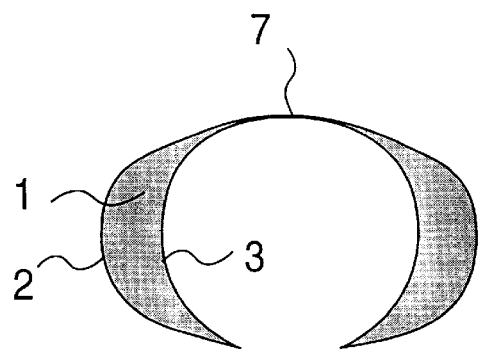
FIG. 4 represents in cross section a variant of the device, where the lateral cheeks are connected together by a thin sheet.

According to another mode of the invention, the two lateral cheeks may be connected by a sheet 7 which is far thinner than the lateral segments 1 as illustrated in FIG. 4.

According to another mode of the invention, the totality of the device may be more closed, and even completely closed (not illustrated) creating a hollow cylinder.

To avoid multiplication of the figures, only examples of embodiments are represented, but the various segments of the device or the strips, may be different in location, shape or thickness according to needs. Thus according to another mode of the invention, the device may include perforations or grooves, not shown, so as to render the device more light and supple.

Main indications are for patients with penile atrophy, either congenital or acquired, with a normal erection. The device allows a lengthening and an increase in diameter of the penis at rest, without changes in physiological erection, since implants cover only a small area of the corpus cavernosum, and therefore do not prevent the increase of circumference of the physiological erection. Additionally, in the case of a moderate deficit of erection without true impotence, the choice of a material of a hardness comprised between about 25 and 50 Shore A, provides a complement of rigidity which is able to allow penetration under satisfactory conditions.

What is claimed is:

1. Penile implant for implantation outside the corpus cavernosum for increasing the total volume of the penis by a concurrent increase of both the length and the diameter, said implant comprising two cheeks independent from one another, said cheeks being adapted to cover the outer lateral sides of the corpus cavernosum without covering the upper and lower sides and each of said cheeks having a crescent-shaped or hemicylindrical vertical cross-section whereby each cheek includes a substantially concave to substantially flat inner surface adapted to cover the outer lateral side of the corpus cavernosum and a substantially convex outer surface, each of said cheeks including a proximal end and a distal end adapted to conform to the anatomy of the sulcus of the glans, said distal end comprising an oblique planar end surface which slants toward the proximal end in a direction from the outer surface to the inner surface.

2. A penile implant in accordance with claim 1 wherein the implant is made from a material having a Shore A hardness of about 25–50.

3. A penile implant in accordance with claim 2 wherein the two cheeks are connected by a thin sheet of material.

4. A penile implant in accordance with claim 2 wherein the implant further includes perforations.

5. A penile implant in accordance with claim 2 wherein the implant comprises a strengthening material.

6. A penile implant in accordance with claim 1 wherein the implant further includes perforations.

7. A penile implant in accordance with claim 6 wherein the two cheeks are connected by a thin sheet.

8. A penile implant in accordance with claim 1 wherein the two cheeks are connected by a thin sheet of material.

9. A penile implant in accordance with claim 1 wherein the implant comprises a strengthening material.

10. A penile implant in accordance with claim 1 wherein the implant includes one or more additions of a material which is able to be secondarily penetrated by neighboring tissue.

* * * * *